United States Patent
Magnusson et al.

(10) Patent No.: US 8,502,969 B2
(45) Date of Patent: Aug. 6, 2013

(54) MINIATURE FLOW-THROUGH CUVETTE AND SPECTROPHOTOMETER CONTAINING THE SAME

(75) Inventors: Gunnar Magnusson, Marviksvägen (SE); Björn Roos, Torsgatan (SE)

(73) Assignee: Boule Medical AB, Stockholm (SE)

( * ) Notice: Subject to any disclaimer, the term of this patent is extended or adjusted under 35 U.S.C. 154(b) by 510 days.

(21) Appl. No.: 12/639,190

(22) Filed: Dec. 16, 2009

(65) Prior Publication Data

US 2011/0141466 A1    Jun. 16, 2011

(51) Int. Cl.
*G01N 1/10* (2006.01)
(52) U.S. Cl.
USPC .......................................... 356/246; 356/440
(58) Field of Classification Search
USPC ................. 356/244, 246, 440; 436/180, 517; 250/227.25, 576; 422/82.08, 82.09
See application file for complete search history.

(56) References Cited

U.S. PATENT DOCUMENTS

| | | | | |
|---|---|---|---|---|
| 3,583,817 | A * | 6/1971 | Rachlis et al. | 356/410 |
| 4,511,251 | A * | 4/1985 | Falcoff et al. | 356/246 |
| 4,823,168 | A * | 4/1989 | Kamahori et al. | 356/246 |
| 5,098,186 | A * | 3/1992 | Bull | 356/246 |
| 5,386,121 | A * | 1/1995 | Barbee et al. | 250/341.8 |
| 5,917,606 | A * | 6/1999 | Kaltenbach | 356/440 |
| 2005/0094127 | A1 * | 5/2005 | O'mahony et al. | 356/39 |
| 2005/0195392 | A1 | 9/2005 | Uchimura et al. | |
| 2009/0046282 | A1 * | 2/2009 | Hong | 356/246 |
| 2009/0153851 | A1 * | 6/2009 | Huemer | 356/246 |

FOREIGN PATENT DOCUMENTS

| | | |
|---|---|---|
| JP | 2008191119 | 8/2008 |
| WO | 2005121750 | 12/2005 |
| WO | WO2007112659 A1 * | 10/2007 |

OTHER PUBLICATIONS

International Search Report and Written Opinion; PCT/SE2010/051275; mailed Mar. 14, 2011.

* cited by examiner

*Primary Examiner* — Tarifur Chowdhury
*Assistant Examiner* — Michael P Lapage
(74) *Attorney, Agent, or Firm* — Latimer IP Law, LLP

(57) ABSTRACT

A miniature flow-through cuvette for spectrophotometric measurement of a liquid sample includes a cuvette body of a transparent material including a first outer surface and an opposing second outer surface, and a flow channel disposed through the cuvette body. The flow channel includes first and second interface segments generally vertically oriented, each having an open exit; a measurement segment interconnecting the first and second interface segments; a first inclined planar inner surface disposed in a turning segment between the first interface segment and the measurement segment, facing the first outer surface; and a second inclined planar inner surface disposed in a turning segment between the second interface segment and the measurement segment, facing the second outer surface. The first and second inclined inner surfaces terminate the measurement segment at opposing ends thereof. Further provided is a spectrophotometer including the miniature flow-through cuvette.

20 Claims, 7 Drawing Sheets

MINIATURE FLOW-THROUGH CUVETTE AND SPECTROPHOTOMETER CONTAINING THE SAME

FIELD OF THE INVENTION

The present invention relates to a miniature flow-through cuvette and a spectrophotometer including such a miniature flow-through cuvette for measurement of a liquid sample, and particularly for spectrophotometric measurement of a blood sample on a blood analyzer.

BACKGROUND OF THE INVENTION

Spectrophotometric measurement of hemoglobin concentration of a blood sample has been used for decades on hematology analyzers. Typically, a blood sample is exposed to a lytic reagent to lyse the red blood cells, and then the released hemoglobin molecules in the sample mixture form a chromogen with a ligand or stabilizer in the reagent. A flow of the sample mixture is delivered through a cuvette in the analyzer, and absorption of the sample mixture is measured and used to calculate hemoglobin concentration of the blood sample.

In the existing hematology analyzers, commonly the measurement window of the cuvette includes two opposing parallel walls disposed along or in parallel with the flow path. A light source and a detector are disposed on opposing sides of the window for measuring absorption of the sample mixture passing through the cuvette. The optical length, namely the distance between the inner side of the two walls of the cuvette, is typically about 10 mm to ensure a sufficient amount of sample for measurement. A known problem in the existing measurement is attachment of micro-bubbles in the sample mixture to the walls of the cuvette, which causes errors in the measurement. Commonly, a large volume of a cleaning solution is used on the analyzers after analysis of each sample to remove and prevent accumulation of micro-bubbles on the surface of the cuvette. However, when the dimensions of the flow path in the cuvette decrease, the ratio of surface area to the volume of the sample mixture increases, and prevention of micro-bubble attachment becomes substantially more difficult.

On the other hand, most automated hematology analyzers have multiple reagents and cleaning solution on board for automated sample preparation and measurements on the instruments. Although these hematology analyzers have known advantages of high capacity, batch sample analysis, automated sample aspiration and preparation, and automated cleaning cycles, these instruments are relatively high cost and use large quantity of reagents, which requires high maintenance of the instruments and reagent inventory management. Therefore, it is difficult to adapt these instruments in a near-patient test environment, such as in the emergency room, where a minimum sample volume and minimum reagent maintenance are required. In near-patient tests, a small volume of blood sample may be collected from fingerstick, and is used to obtain a complete blood count (CBC) on an analyzer. As such, substantially reduced reagent volumes are used to maintain desired cell concentrations to ensure accurate measurement.

In the recent years, disposable cassette containing reagents for analysis of one sample and blood analyzers adapted to use the disposable cassettes have been developed for meeting such a need in near-patient testing. The disposable cassette contains pre-filled reagents with predetermined volumes designated for a complete analysis of one sample. To accommodate for the small sample and reagent volumes, the fluid volume in the cuvette used for hemoglobin measurement on a hematology analyzer needs to be reduced. This significantly increases the ratio of surface area of the flow path to the volume of the sample mixture, and renders extremely difficult to control micro-bubble formation and attachment within the cuvette when the sample mixture passes through and when it is measured in the cuvette. Moreover, it is also technically challenging to remove micro-bubbles attached to or accumulated in the cuvette using a small volume of a cleaning solution provided in the cassette only.

Therefore, there exists a clear need for a spectrophotometer using a cuvette with a minimum fluid volume for providing an accurate measurement of hemoglobin concentration of a blood sample and meeting requirements of in-vitro clinical diagnosis. Furthermore, it is strongly desirable to provide a miniature cuvette that can effectively minimize micro-bubble formation and accumulation within the cuvette and minimize reliance on the amount of cleaning solution for removal of the micro-bubbles.

SUMMARY OF THE INVENTION

In one aspect, the present invention is directed to a miniature flow-through cuvette for spectrophotometric measurement of a liquid sample. In one embodiment, the miniature flow-through cuvette comprises a cuvette body of a transparent material including a first planar outer surface and an opposing second planar outer surface; and a flow channel disposed through the cuvette body. The flow channel comprises a first interface segment and a second interface segment, oriented generally in a direction of a vertical axis of the cuvette body, each having an open exit; a measurement segment interconnecting the first and second interface segments; a first inclined planar inner surface disposed in a first turning segment between the first interface segment and the measurement segment, facing the first planar outer surface; and an opposing second inclined planar inner surface disposed in a second turning segment between the second interface segment and the measurement segment, facing the second planar outer surface. The first and second inclined planar inner surfaces terminate the measurement segment at opposing ends thereof. The inclined angle of each of the first and second inclined planar inner surfaces relative to the vertical axis is from about 15 to about 65 degrees. The first and second interface segments and the measurement segment have a substantially same diameter. In a further embodiment, the first outer surface and the second outer surface are inclined relative to the vertical axis of the cuvette body.

In another embodiment, the flow-through cuvette has a cuvette body formed of a first and a second body blocks. The first body block includes the first planar outer surface and an opposing joining surface, the first interface segment, and a first portion of the measurement segment of the flow channel including the first inclined planar inner surface. The second body block including the second planar outer surface and an opposing joining surface, the second interface segment, and a second portion of the measurement segment of the flow channel including the second inclined planar inner surface. The first and second body blocks are joined together with the joining surfaces of the body blocks against each other, and the first and second portions of the measurement segment aligned with each other. Each of the first and second body blocks comprises a sealing groove on the joining surfaces of the body blocks, surrounding respective portion of the measurement segment of the flow channel; and a sealing member is disposed in the sealing grooves.

In a further aspect, the present invention is directed to a spectrophotometer for measurement of a liquid sample. The spectrophotometer comprises the miniature flow-through cuvette described above; a light source disposed next to the first planar outer surface and adapted to emit an incident light beam through the measurement segment of the flow channel; and a photo detector disposed next to the second planar outer surface and adapted to receive a transmitted light through the measurement segment of the flow channel. The light source comprises a housing having a chamber of a dark interior and a light outlet disposed against the first planar outer surface of the cuvette body, and a light bulb disposed within the housing, facing the light outlet. The center of the light outlet of the light source is optically aligned with a central axis of the measurement segment of the flow channel of the flow-through cuvette. The photo detector comprises a detector housing having a chamber of a dark interior and a light inlet disposed against the second planar outer surface of the cuvette body, and a sensor disposed within the detector housing. The center of the light inlet of the photo detector is optically aligned with a central axis of the measurement segment of the flow channel of the flow-through cuvette.

The advantages of the present invention will become apparent from the following description taken in conjunction with the accompanying drawings showing exemplary embodiments of the invention.

BRIEF DESCRIPTION OF THE DRAWINGS

It is noted that in the drawings like numerals refer to like components.

DETAILED DESCRIPTION OF THE INVENTION

Figure 1:
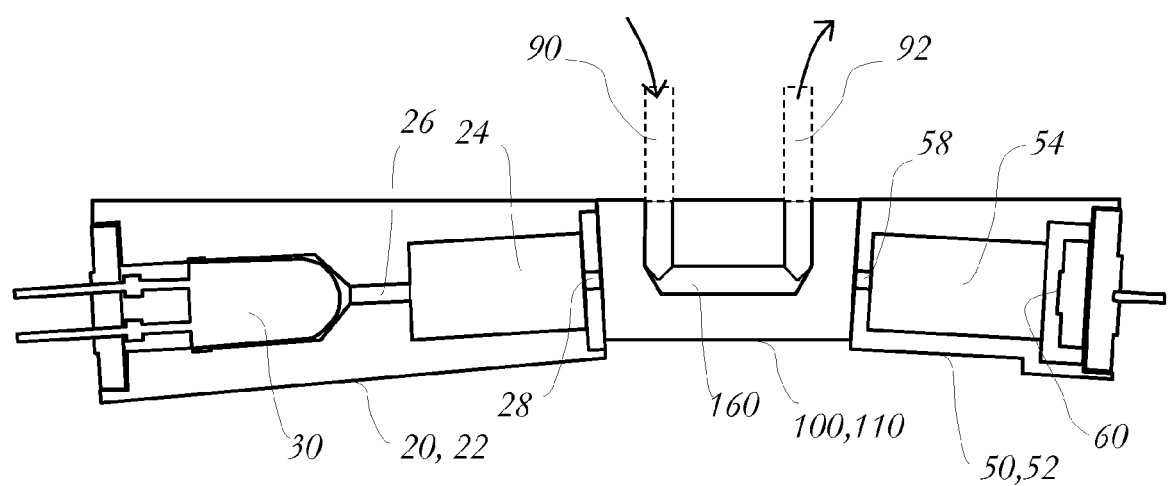
FIG. 1 is an illustrative view of a spectrophotometer of the present invention comprising a miniature flow-through cuvette in one embodiment of the present invention.

In one aspect, the present invention provides a spectrophotometer that comprises a miniature flow-through cuvette for measurement of a liquid sample flowing therethrough. As shown in FIG. 1, in one embodiment spectrophotometer 10 includes a miniature flow-through cuvette 100, a light source 20, and a photo detector 50.

Figure 2A:
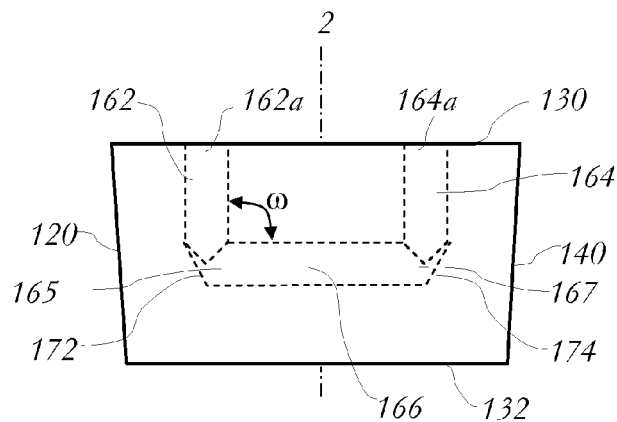
FIGS. 2A, 2B and 2C are the front, side and top views of the flow-through cuvette shown in FIG. 2, respectively.
Figure 2B:
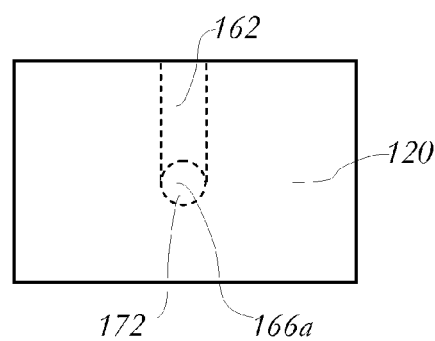
Figure 2C:
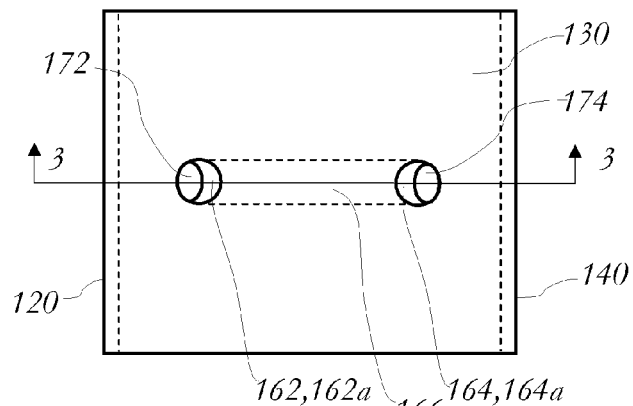
Figure 2:
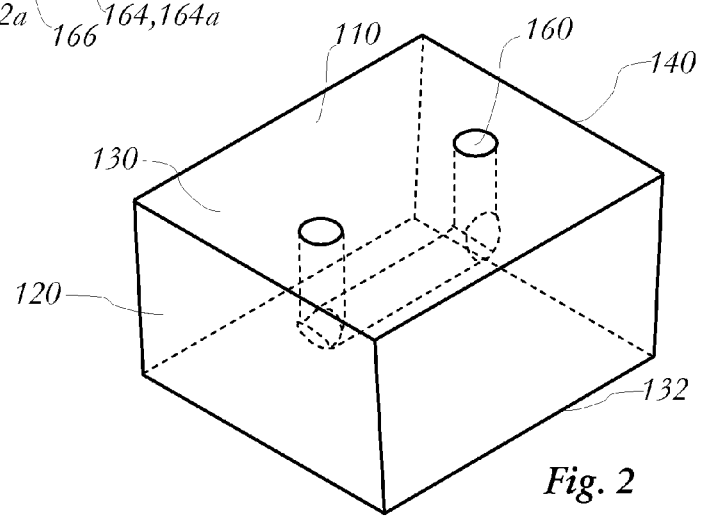
FIG. 2 is a perspective view of the flow-through cuvette in the spectrophotometer shown in FIG. 1.
Figure 3:
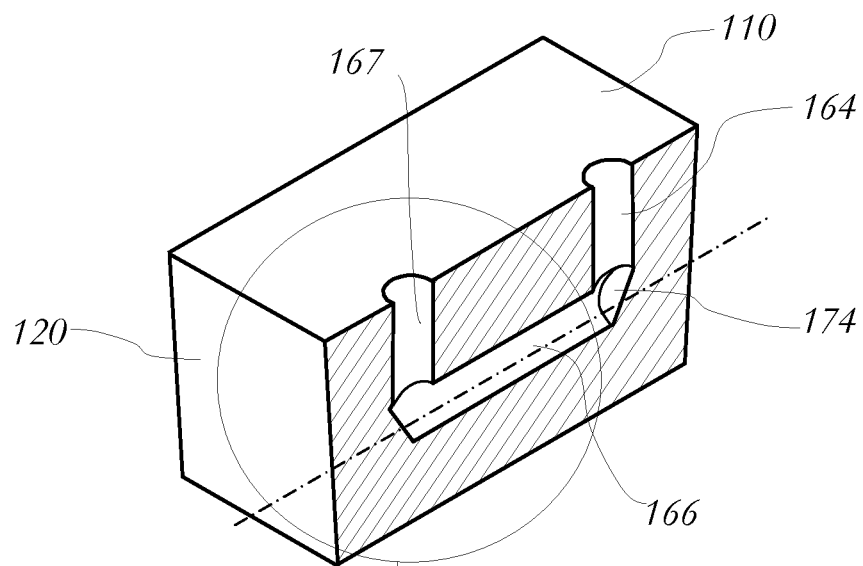
FIG. 3 is a perspective cross-sectional view of the flow-through cuvette shown in FIG. 2, along line 3-3 in FIG. 2C.
Figure 3A:
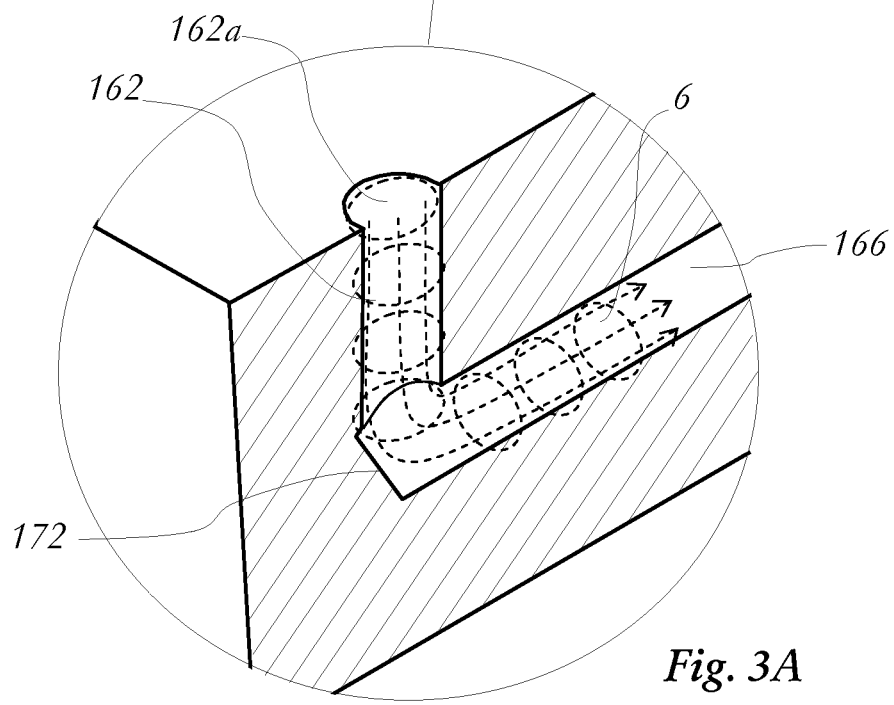
FIG. 3A is an enlarged partial view of FIG. 3, showing a flow of a liquid sample through the flow channel of the cuvette.

FIGS. 2 to 3A show a miniature flow-through cuvette 100 in one embodiment of the present invention. The flow-through cuvette 100 has a cuvette body 110 made of a transparent material. Cuvette body 110 has an upper side 130, a bottom side 132, a first outer surface 120, and an opposing second outer surface 140. Both the first and second outer surfaces, or at least the areas of the first and second outer surfaces in line with the measurement segment of the flow channel as described hereinafter, are planar. In the exemplary embodiment shown, both first and second outer surfaces 120 and 140 are inclined relative to the vertical axis 2 of cuvette body 110. However, the outer surfaces may also be straight depending on the material and configurations of other related structural components of the cuvette as described hereinafter.

Flow-through cuvette 100 is miniature in size, particularly suitable for measurement of a small volume of a liquid sample. In one exemplary embodiment, cuvette body 110 has a length (between outer surfaces 120 and 140 at their upper ends) from about 7 to about 30 millimeters (mm), preferably from about 10 to about 20 mm, a height from about 4 to about 15 mm, and a thickness (front to rear) from about 4 to about 15 mm.

As shown in FIGS. 2-2C, flow-through cuvette 100 has a flow channel 160 disposed within and through cuvette body 110. Flow channel 160 includes a first interface segment 162 having an open exit 162a, a second interface segment 164 having an open exit 164a, and a measurement segment 166 located between and interconnecting interface segments 162 and 164 at their ends opposing open exits 162a and 164a. The first and second interface segments are oriented generally in the direction of the vertical axis 2 of the cuvette body. In a blood analyzer or other measurement device that includes spectrophotometer 10 adapted to measure absorption of a liquid sample carried in conduits of the device, open exits 162a and 164a of flow channel 160 are fluidly connected to the conduits of the device, as illustrated by conduits 90 and 92 in FIG. 1. Either the first interface segment 162 or the second interface segment 164 can be used as an inlet, an outlet, or both, of the flow channel 160, depending on the flow direction(s) present in a sample measurement process. In an example flow direction illustrated in FIGS. 1 and 3A, a liquid sample to be measured flows into flow channel 160 of cuvette 100 through conduit 90 and exits the cuvette to conduit 92 (see arrows in FIG. 1).

Preferably, both interface segments 162 and 164 and measurement segment 166 have a circular cross section with a substantially same diameter. This facilitates a uniform flow rate throughout flow channel 160, and the uniform flow rate effectively reduces micro-bubble formation within flow channel 160. Typically, the diameter of both interface segments and the measurement segment can be from about 0.8 to about 4.0 mm, preferably from about 1.4 to about 2.4 mm. Moreover, to ensure a sufficient optical length for spectrophotometric measurement of a liquid sample within the cuvette, measurement segment 166 has a length from about 4 to about 25 mm, preferably from about 7 to 13 mm. In the miniature cuvette, flow channel 160 may have a volume from about 3 up to 250 microliter (μl), preferably from about 10 to about 60 μl, more preferably about 20 to about 40 μl.

As shown in FIG. 2A, the lower ends of the first and second interface segments 162 and 164 are directly connected with the opposing ends of the measurement segment 166. The portions of the flow channel at which the measurement segment and the interface segments are joined and at which one segment turns to the other are referred to as the first and second turning segments 165 and 167, respectively. Flow channel 160 includes a first inclined planar inner surface 172 in the first turning segment 165, facing the first outer surface 120, and a second inclined planar inner surface 174 in the second turning segment 167, facing the second outer surface 140. The first and second inclined planar inner surfaces 172, 174 terminate the measurement segment 166 at its opposing ends. The degree of inclination of the first and second inclined inner surfaces 172, 174 from the vertical axis 2 is herein referred to as a first inner inclined angle and a second inner inclined angle, respectively. The degree of inclination of the first and second inclined inner surfaces are determined based on desired flow characteristics and light path of the spectrophotometer for optical measurement of a liquid sample in the measurement segment 166 of flow channel 160, as described in details hereinafter.

The first and second inner inclined angles may be the same and may also be different. Preferably, the first and second inner inclined angles are in a range from about 15 to about 65 degrees, preferably from about 30 to about 50 degrees, relative to the vertical axis of the cuvette body. As can be appreciated from FIG. 2A, the inclined planar inner surfaces 172 and 174 eliminate the sharp turn corners between the two interface segments 162, 164 and measurement segment 166, and eliminate dead spots in the flow path. It has been found that when the inclined inner angle is less than 15 degrees, it is less effective in preventing micro-bubble formation, and while when the inclined inner angle is higher than 65 degrees, a substantial light scattering of the incident light of the spectrophotometer may occur at the inclined inner surface. As illustrated in FIG. 3A, because of elimination of the sharp angles in the turning segments, a smooth flow is maintained when a liquid sample passes through flow channel 160. Moreover, as described above the interface segments and the measurement segment have a substantially same diameter. As such, no substantial flow restriction is present throughout the entire flow channel 160. Such a structural feature minimizes micro-bubble formation when a liquid sample passes through the flow channel, and effectively prevents micro-bubble accumulation in dead spots which are the sharp turn corners where no flow or a very low flow rate is present.

The inclined inner surfaces 172 and 174, and the outer surfaces 120 and 140, or at least the areas of the out surfaces corresponding to the cross section of measurement segment 166, are polished for optical measurement. The light path through the flow-through cuvette and the relationship between the inclined inner surface and the outer surface are illustrated using flow-through cuvette 100 in FIGS. 4 and 5.

Figure 4:
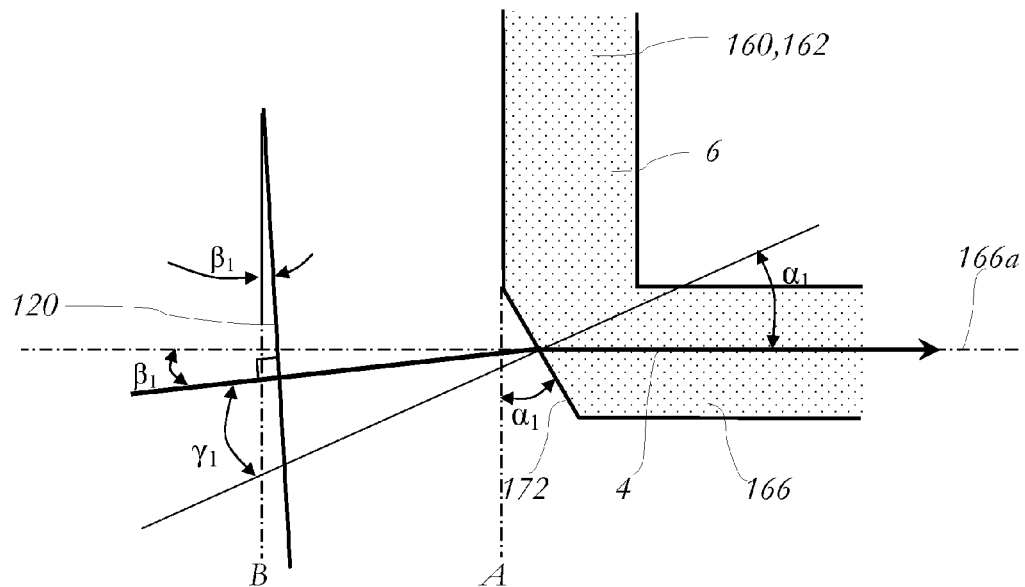
FIG. 4 is an illustrative view showing the relationship of the first outer surface, the first inclined inner surface and the light path at one side of the flow-through cuvette in one embodiment of the present invention.

FIG. 4 shows an illustrative enlarged partial view of flow-through cuvette 100 shown in FIG. 2, where only the first outer surface 120 and the first inclined inner surface 172 of the cuvette are shown, with a liquid sample 6 present in flow channel 160. As noted previously, in the embodiment shown the first and second out surfaces 120, 140 are also inclined. The degree of inclination of the first and second outer surfaces 120 and 140 relative to the vertical axis 2 of cuvette body 110 is herein referred to as a first outer inclined angle and a second outer inclined angle, respectively. In FIG. 4, line 4 denotes the light path of the light beam as it propagates through the cuvette body and liquid sample 6 in the measurement segment 166 of flow channel 160 toward the photo detector. Angle $\alpha_1$ is the first inner inclined angle of the first inclined inner surface 172 relative to the vertical axis 2 of the cuvette body, and angle $\beta_1$ is the first outer inclined angle of the first outer surface 120 from the vertical axis 2 of the cuvette body, respectively. It is noted that in FIG. 4, reference line A and line B are both in parallel to the vertical axis 2. Angle $\gamma_1$ is the angle of incidence of the light beam at the first inclined inner surface 172. As can be appreciated from FIG. 4, angle $\alpha_1$ is also the angle of the refracted or transmitted light at the interface between the cuvette body and the liquid sample.

As shown, preferably the light path 4 is aligned with the central axis 166a of measurement segment 166 of flow channel 160, which minimizes reflection of the light beam within the measurement segment. As described above, the first inner inclined angle $\alpha_1$ is in a range from about 15 to about 65 degree from the vertical axis 2 of the cuvette body. Once the first inner inclined angle $\alpha_1$ is determined, the first outer inclined angle $\beta_1$ can be determined using Snell's law. According to Snell's law, the incidence angle $\gamma_1$ and the angle $\alpha_1$ of the refracted or transmitted light at the first inclined inner surface 172 has a relationship defined by the following equation:

$$n_c \cdot \sin \gamma_1 = n_s \cdot \sin \alpha_1$$

wherein $n_c$ is the refractive index of the material of the cuvette body, and $n_s$ is the refractive index of the liquid sample. Once the material used for making the cuvette body is determined, $n_c$ is known. For example, refractive indices of UV-grade fused silica and acrylic glass are 1.46 and 1.49, respectively. If the liquid sample to be tested is aqueous, the refractive index of water can be used as an estimate, which is 1.33.

Since both refractive indices are known and the first inclined inner angle $\alpha_1$ is also known, the incidence angle $\gamma_1$ can be calculated using the above equation. As further shown in FIG. 4, $\alpha_1 = \beta_1 + \gamma_1$. As such, the first outer inclined angle $\beta_1$ can be determined. As can be readily understood from FIG. 4, because of the optical relationship, the first inclined inner angle and the first inclined outer angle of flow-through cuvette 100 are generally not the same. In one exemplary embodiment, the cuvette body is made of a material having a refractive index of 1.48 and the liquid sample has a refractive index of 1.34, and the first inclined inner angle $\alpha_1$ is about 30°, the first inclined outer angle $\beta_1$ is about 3°, and incidence angle $\gamma_1$ is about 27°. As such, when flow-through cuvette 100 is installed in the spectrophotometer, the light beam and the cuvette are optically aligned such that light path 4 is aligned with central axis of the measurement segment 166 of flow channel 160.

Figure 5:
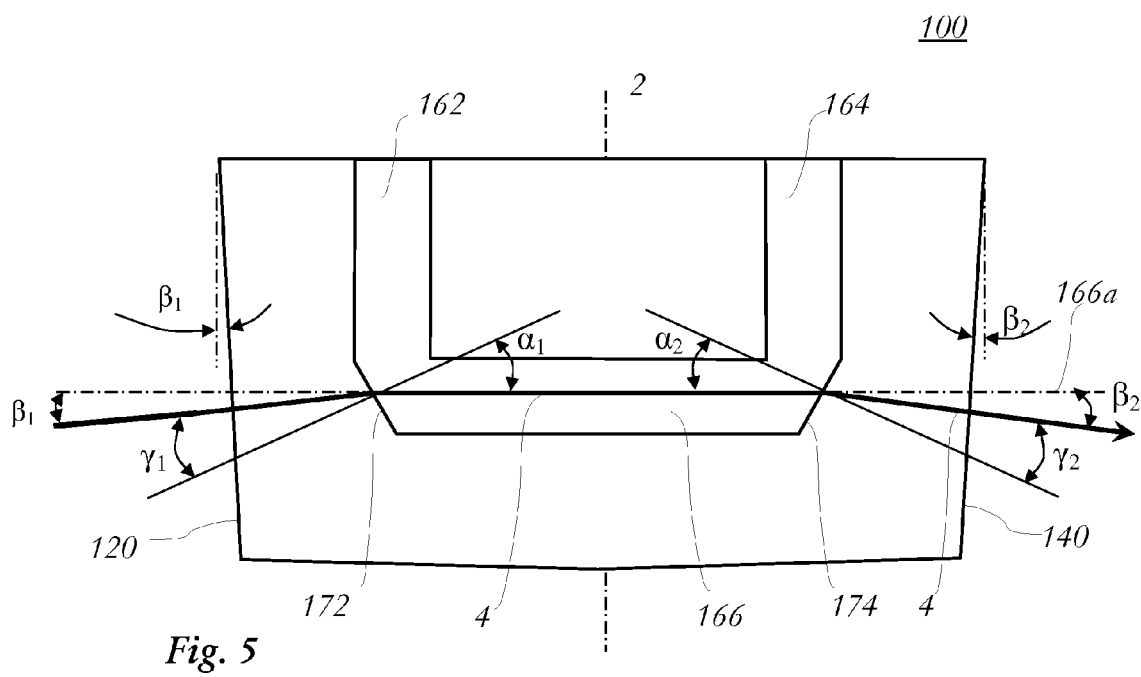
FIG. 5 is an illustrative view of the light path through the flow-through cuvette shown in FIG. 2.

As illustrated in FIG. 5, in the embodiment shown flow-through cuvette 100 has the first and second inclined inner surfaces 172, 174 and the first and second outer surfaces 120, 140 substantially symmetric to the vertical axis 2. In other words, the first and second inner inclined angles $\alpha_1$ and $\alpha_2$ are the same, and the first and second outer inclined angles $\beta_1$ and $\beta_2$ are the same. Moreover, when the cuvette body is made of one single material, the angle $\gamma_2$ of the refracted light at the interface between the liquid sample and the cuvette, i.e., at the second inclined inner surface 174, is the same as the incidence angle $\gamma_1$. The light exiting from the cuvette is then detected by the photo detector disposed at the second outer surface 140 of the cuvette, as further described hereinafter.

As can be seen from FIG. 5, the optical length of the flow-through cuvette 100 is the length of measurement segment 166. With the preferred optical alignment described above, the optical length is approximately the distance between the first and second inclined inner surfaces along the central axis 166a of the measurement segment (see FIGS. 4 and 2B). Herein, the central axis of the measurement segment refers to the longitudinal axis at the cross-section center of the measurement segment. It should be understood that the incident light beam has a certain diameter, for example in one embodiment the light beam has a diameter about 1 mm. Since surfaces 172 and 174 are inclined, the distance between the first and second inclined inner surfaces along the central axis of the measurement segment is an average of the optical length. The wall between the inclined inner surface and respective outer surface is preferably thin, to avoid loss of light across the wall. In one embodiment, the thickness of the wall is from about 1 mm to about 5 mm.

It is noted that the light path of flow-through cuvette 100 is distinctly different from that in the traditional spectrophotometer used for measuring a liquid sample passing through a cuvette. In the latter, the light path is traverse to the flow path or the flow direction of the liquid sample passing through the cuvette, and the optical length is the inner diameter, or width of the cuvette. While in the flow-through cuvette of the present invention, the light path is in parallel with the flow direction within the measurement segment, and the optical length is the length of the measurement segment, rather than the diameter thereof. As can be appreciated, since flow-through cuvette 100 is a miniature cuvette and the diameter of the measurement segment is only from about 0.8 to about 4.0 mm, the arrangement of the light path in parallel with, instead of transverse to, the longitudinal axis of the measurement segment provides a sufficient optical length to ensure accurate absorption measurement. With this structure, the volume of the sample mixture can be substantially reduced without decreasing the optical length for the spectrophotometric measurement.

As shown in FIG. 1, in one embodiment light source 20 includes a housing 22 and a light bulb 30 disposed at rear portion of the housing. Housing 22 includes a chamber 24 with a dark colored interior, an inlet 26 and a light outlet 28 aligned with inlet 26. Preferably, both inlet 26 and light outlet 28 are circular. Light bulb 30 is disposed next to inlet 26, which has a diameter substantially less than the diameter of the light bulb. The inlet 26 functions as a gate, only permits a central light beam entering chamber 24, and exiting from light outlet 28. Chamber 24 has a dark interior, such as black, which absorbs residual stray light from the light beam. Light outlet 28 is disposed against the first outer surface 120 of flow-through cuvette 100, which permits the light beam exited from the outlet directly impinging on the first outer surface 120, without interference from ambient stray light. Light outlet 28 has a dimension less than the dimension or the overall area of the first inclined inner surface 172 of flow-through cuvette 100, and the center of the light outlet 28 is optically aligned with the central axis of measurement segment 166 of flow channel 160 of the cuvette. Herein, the dimension of the light outlet 28 refers to the cross sectional dimension of the outlet transverse to the light beam. In one exemplary embodiment, the diameter of circular inlet 26 and light outlet 28 is about 1 mm, and the diameter of measurement segment 166, which is the diameter of the inclined inner surface (see FIG. 2B), is about 2 mm. As can be appreciated, the structure of the light source produces a centered incidence light beam to the measurement segment of the cuvette.

As further shown in FIG. 1, in one embodiment photo detector 50 includes a housing 52 and an optical sensor 60 disposed at the rear portion of the housing. Housing 52 includes a chamber 54 and a light inlet 58. Light inlet 58 has a dimension less than the dimension of the second inclined inner surface 174 of cuvette 100, and the center of light inlet 58 is optically aligned with the central axis of the measurement segment 166 of the cuvette. Herein, the dimension of the light inlet 58 refers to the cross sectional dimension of the inlet transverse to the transmitted light. Light inlet 58 is disposed against the second outer surface 140, which causes the transmitted light exiting from the cuvette directly entering chamber 54. Chamber 54 has a dark interior, such as black, which absorbs stray light entering into the chamber. As such, only the centered light impinges on and detected by optical sensor 60. The intensity of the transmitted light through the liquid sample in the measurement segment 166 of cuvette 100 is inversely proportional to the concentration of the substance that absorbs the light. The concentration of such a substance in the liquid sample can be calculated according to Beer's law.

Various commercially available light bulbs can be used for the purpose of the present invention. Suitable examples include, but not limited to, diode, laser, and lamp with a filter with a predetermined wavelength. Preferably, a LED light bulb is used. In one example, a green LED with a wavelength of 525 nm from Nichia Corporation (Tokyo, Japan) is used. On the other hand, various optical sensors can be used in the photo detector of spectrophotometer 10. Suitable examples include, but not limited to, photodiode and charge-coupled device (CCD). In one exemplary embodiment, a S1087/S1133 series ceramic package photodiode with low dark current from Hamamatsu Photonics K.K. (Hamamatsu city, Japan) is used. In this type of photodiode, ceramic package used is light-impervious, therefore no stray light can reach the active area from the side or backside. This allows reliable optical measurements in the visible to near infrared range over a wide dynamic range from low light levels to high light levels.

Figure 6:
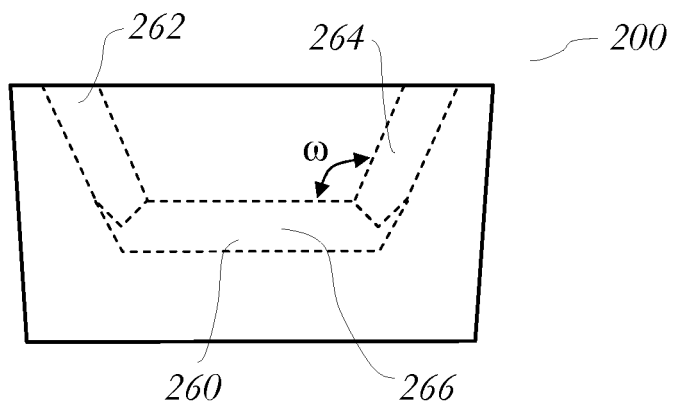
FIG. 6 is a front view of a flow-through cuvette in a further embodiment of the present invention.

In the flow-through cuvette 100 described above, the longitudinal axes of the interface segments 162 and 164 are about 90 degree from the longitudinal axis of the measurement segment 166 (angle ω in FIG. 2A). However, it should be understood that the interface segments can be positioned in a broad angle range relative to the measurement segment. Typically, the longitudinal axes of the interface segments can be from about 80 to about 135 degrees from the longitudinal axis of the measurement segment, as expressed by angle ω in FIG. 2A. FIG. 6 shows a flow-through cuvette 200 in an alternative embodiment of the present invention. As shown in flow-through cuvette 200, the first and second interface segments 262 and 264 of flow channel 260 are about 120 degrees from the longitudinal axis of the measurement segment 266 (see angle ω).

It has been found that the interface segments oriented generally in the vertical direction is more advantageous. With such an orientation, any micro-bubble carried in the liquid sample flowing through channel 160 tends to lift upwardly into the interface segments. This avoids accumulation of micro-bubbles in the measurement segment and prevents interference caused by the micro-bubbles to the absorption measurement.

Figure 7:
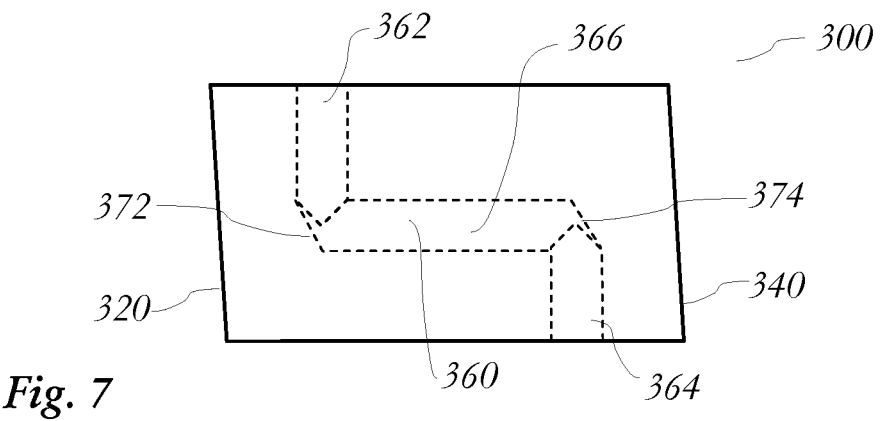
FIG. 7 is a front view of a flow-through cuvette in another embodiment of the present invention, where the first and second interface segments are in opposing directions.

Furthermore, the two interface segments may also have different orientations. For example, the first interface segment may be 120 degrees from the measurement segment, and the second interface segment may be 90 degrees from the measurement segment. In a further embodiment shown in FIG. 7, flow-through cuvette 300 has the first and second interface segments 362 and 364 in opposing directions of the measurement segment 366. With this embodiment, the liquid sample is typically fed into flow channel 360 from the second interface segment 364 upwardly.

Furthermore, in the flow-through cuvette 100 described above, the first and second inclined inner surfaces 172, 174 and the first and second outer surfaces 120, 140 are substantially symmetric to the vertical axis 2 of the cuvette body. However, it should be understood that the first and second inner inclined angles $\alpha_1$ and $\alpha_2$ can also be different, and the first and second outer inclined angles $\beta_1$ and $\beta_2$ can be different. In the embodiment shown in FIG. 7, both the first and second inclined inner surfaces 372 and 374 are inclined in the same general direction, instead of in opposing directions as in cuvette 100. Consequently, both the first and second outer surfaces 320 and 340 are also inclined in the same general direction, instead of in opposing directions, due to the optical relationship described above according to the Snell's law. Moreover, if the cuvette body is made of different materials on two sides, for example the portion of the cuvette including the first outer and inner surfaces is made of one material and the portion of the cuvette including the second outer and inner surfaces is made of another material, the respective inclined angles can be different because the difference in refractive index of the materials.

Figure 8:
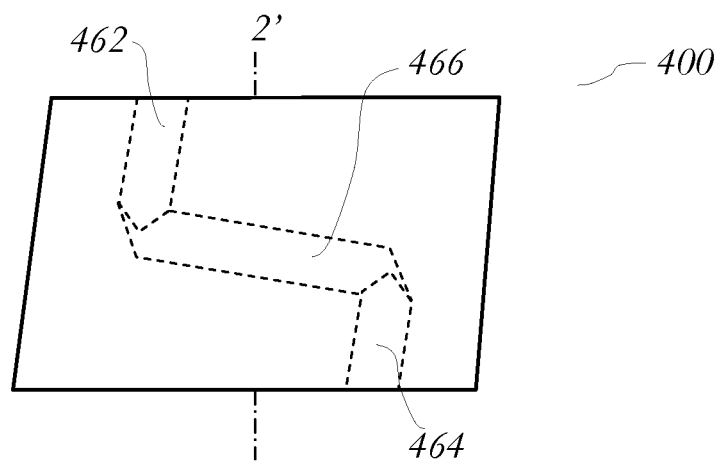
FIG. 8 is a front view of a flow-through cuvette in yet a further embodiment of the present invention, where all segments of the flow channel are tilted relative to the vertical axis of the cuvette body.

Moreover, depending on the desired flow characteristics in a measurement device the measurement segment of the flow channel may be not horizontal as that shown in FIG. 2, instead the measurement segment may be tilted as illustrated in FIG. 8. As shown in FIG. 8, flow-through cuvette 400 has the first and second interface segments 462 and 464 in opposing directions of the measurement segment 466. Furthermore, both first and second interface segments and the measurement segment are tilted relative to the vertical axis 2' of the cuvette body. However, the first and second inclined inner angles and the first and second outer inclined angles can be determined with the same principles described above in reference to flow-through cuvette 100. In this configuration, the light source and the photo detector may not be on the same plane, however, both can be positioned to maintain optical alignment with the measurement segment of the flow channel of the cuvette. In an alternative embodiment, the cuvette body itself can be tilted for a certain degree if needed. It is noted that when the cuvette body is tilted, the vertical axis 2 (see FIG. 2) of the cuvette body is tilted away from the absolute vertical direction. In this case, the longitudinal axis of the interface segments are preferably tilted no more than 45 degrees from the absolute vertical direction.

The cuvette body can be made of a transparent material suitable for spectrophotometric measurement. Suitable materials include, but not limited to, quartz, acrylic glass, poly carbonate, nylon or other transparent materials compatible with chemicals contained in the liquid sample to be tested. Preferably, the material is suitable for plastic molding, which facilitates convenient manufacturing of the cuvette. As described above, both the inclined inner surfaces and the outer surfaces are polished for optical measurement.

Figure 9:
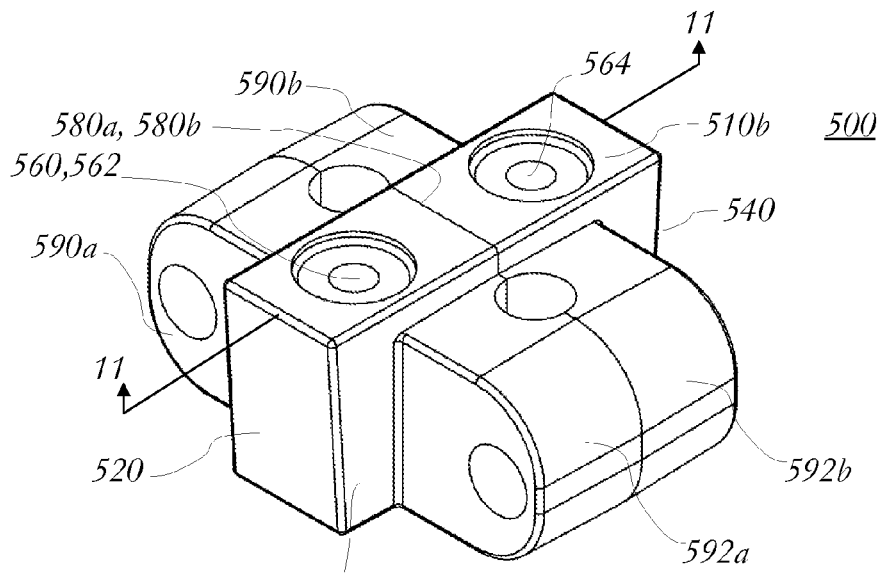
FIG. 9 is a perspective view of the flow-through cuvette in a further embodiment of the present invention.
Figure 10:
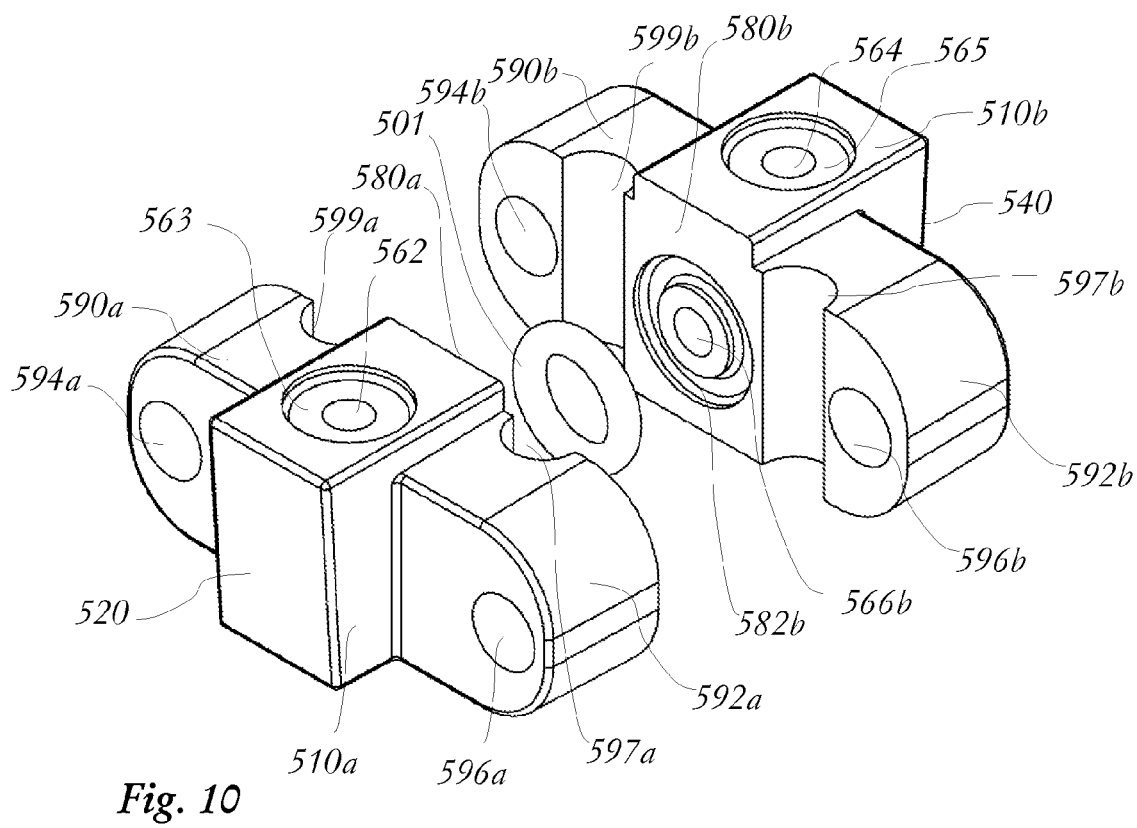
FIG. 10 is an exploded view of the flow-through cuvette shown in FIG. 9.
Figure 11:
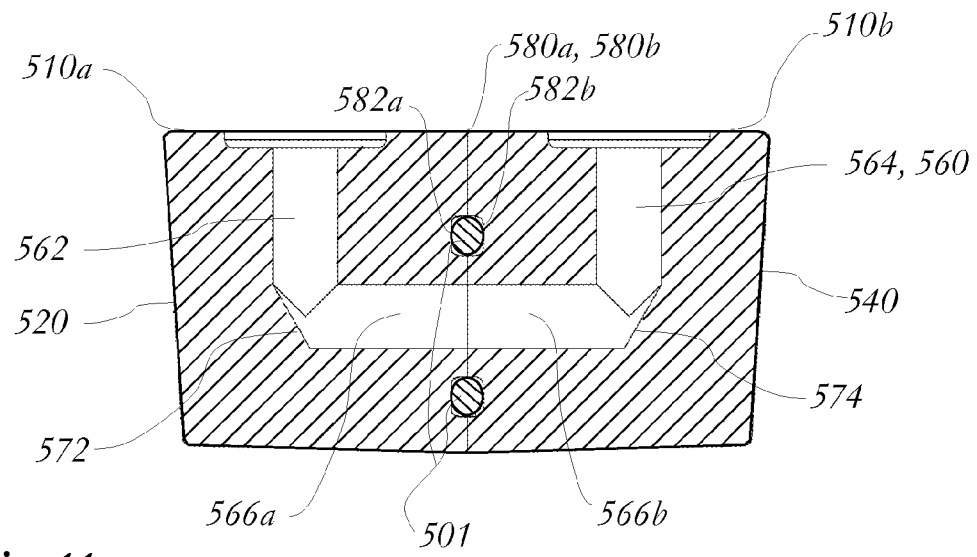
FIG. 11 is a cross-sectional view of the flow-through cuvette shown in FIG. 6, along line 11-11 of FIG. 9.

FIGS. 9-11 illustrate a flow-through cuvette 500 in a further embodiment of the present invention. As shown, flow-through cuvette 500 has a cuvette body that is formed by joining a first body block 510a and a second body block 510b. The first body block 510a includes first outer surface 520, an opposing joining surface 580a, first interface segment 562, and a first portion of the measurement segment 566a of flow channel 560 including the first inclined inner surface 572. The second body block 510b includes second outer surface 540, an opposing joining surface 580b, second interface segment 564, and a second portion of the measurement segment 566b including the second inclined inner surface 574. The first and second portions 566a, 566b of the measurement segment in the two body blocks have a same diameter. The first and second body blocks 510a and 510b are fastened together with joining surfaces 580a and 580b disposed against each other, and the first and second portions of the measurement segment 566a, 566b axially aligned with each other to form a continuous flow channel 560.

As shown in FIGS. 10 and 11, each body block includes a sealing groove 582a, 582b on its joining surface 580a, 580b, surrounding the respective portion of the measurement segment of the flow channel. Flow-through cuvette 500 includes a sealing member 501, such as an O-ring, disposed in the two opposing sealing grooves 582a, 582b. When the two body blocks are fastened, the O-ring is compressed around the interface between the first and second portions 566a, 566b of the measurement segment to ensure a sealed connection of the flow channel 560, see the cross-sectional view in FIG. 11. Preferably, the sealing member is made of an elastic material, which is chemically compatible with the liquid sample to be tested within the cuvette.

Figure 9B:
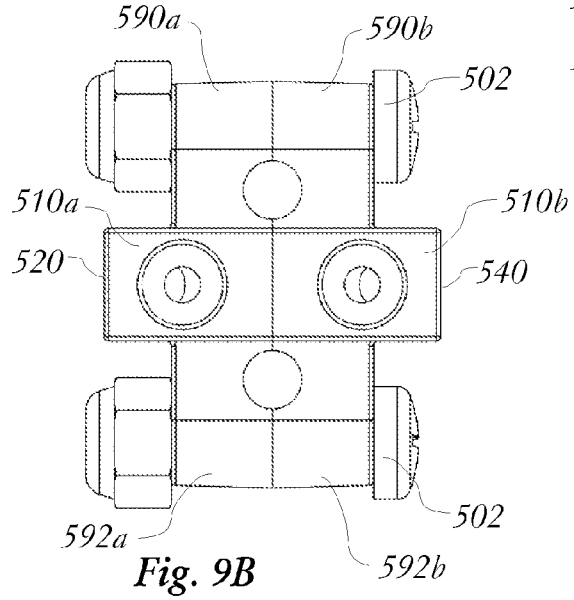
FIG. 9B is a top view of the flow-through cuvette shown in FIG. 9 with a pair of bolts fastening the two body blocks.
Figure 9A:
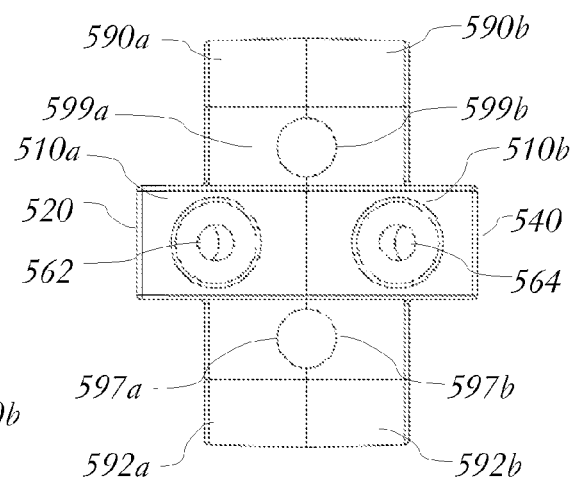
FIG. 9A is a top view of the flow-through cuvette shown in FIG. 9.

As shown, the first body block 510a includes a pair of flange 590a and 592a, extending from the body block from the two sides transverse to the first outer surface 520. Each of the flanges 590a and 592a includes a horizontally oriented through-hole 594a and 596a, respectively. Similarly, the second body block 510b includes a pair of flange 590b and 592b, extending from the body block from the two sides transverse to the second outer surface 540. Each of the flanges 590b and 592b includes a horizontally oriented through-hole 594b and 596b, respectively. When the flow-through cuvette is assembled, the two body blocks are joined together by fasten means. Various suitable fasten means can be used, such as bolts, screws, pins, adhesives, and other known fasten means. When bolts, screws, or pins are used, they can be fastened utilizing the through holes 594a, 596a, 594b and 596b. FIG. 9B shows a pair of bolts 502 are used to fasten the two body blocks together in such a manner.

As further shown, each flange of each body block further includes a vertically oriented recess 597a, 597b, 599a, 599b, opposing a respective recess of the opposing body block. When the two body blocks are joined together, the recesses form a pair of vertical through-holes on two sides of the formed cuvette body. When installed into a spectrophotometer, flow-through cuvette 500 can be fastened to a support in the associated measurement device by fasten means through these two vertical through-holes.

As can be appreciated from the cross-sectional view in FIG. 11, flow-through cuvette 500 has a substantially same flow channel structure and the inclined inner surfaces and outer surfaces as those in flow-through cuvette 100 described above. In other words, in the embodiment shown the first and second body blocks are substantially a mirror image of each other, symmetric relative to the vertical axis of the cuvette. As shown, after joining the first and second body blocks 510a and 510b together as described above, a continuous flow channel 560 is formed. Since the first and second portions 566a and 566b of the measurement segment have the same diameter and the two portions are co-axial, the interior of the measurement segment is a smooth cylinder without interruption. The relationships between the first inclined inner surface 572 and the first outer surface 520, and between the second inclined inner surface 574 and the second outer surface 540 are same as those described in flow-through cuvette 100 above. As such, the optical alignments between the light source and the cuvette, and between the cuvette and the photo detector are the same as described above in reference to flow-through cuvette 100. Moreover, in one embodiment, the two joining surfaces 580a and 580b can be further painted with a dark color, such as black. This may further reduce potential scattering along the light path.

As can be appreciated, the two joining surfaces 580*a* and 580*b* of the two body blocks are in transverse to the longitudinal axis of the measurement segment. This configuration ensures that both inclined inner surfaces, as well as their corresponding outer surfaces, have an uninterrupted integral structure. As such, the two body blocks can be conveniently produced and assembled, without affecting optical property of the cuvette described above. Moreover, the interface between the first and second portions 566*a*, 566*b* of the measurement segment of the flow channel have a substantially small dimension, which eases alignment between the two blocks and can be sealed conveniently and reliably by the O-ring.

As further shown in FIG. 10, both the first and second body blocks have a circular recess 563, 565 on the top surface surrounding the open exit of the first and second interface segments 562 and 564, respectively. When flow-through cuvette 500 is installed in a measurement device, the first and second interface segments 562 and 564 are connected to two fluid conduits of the device, respectively, as illustrated in FIG. 1. The recess 563, 565 surrounding the open exit of each of the interface segments is used to receive a sealing member and/or a fasten member adapted to join a conduit with the interface segment of the flow channel of the cuvette, and to seal the connection interface therebetween. The two body blocks can be produced using plastic molding. Since the first and second body blocks are a mirror image of each other, both blocks can be made using a single mold.

The spectrophotometer of the present invention can be used for spectrophotometric measurement of a liquid sample in various applications, particularly for a small volume of a sample. In one embodiment, the spectrophotometer is used for measuring hemoglobin concentration of a biological sample, such as peripheral blood or urine. In one exemplary embodiment, the spectrophotometer including the flow-through cuvette 500, light source 20 and photo detector 50 is integrated in a hematology analyzer, with the first and second interface segments 562, 564 of the flow channel connected to a first and a second conduit within the hematology analyzer, respectively.

In hemoglobin measurement of a blood sample on such a hematology analyzer, a small aliquot of a blood sample, from about 1 to about 10 μl, is mixed with a predetermined volume of a lysing reagent which contains a lytic agent and a hemoglobin ligand or stabilizer, at a dilution ratio from about 1:200 to about 1:1000, preferably from about 1:300 to about 1:500. Upon mixing, the red blood cells in the sample mixture are lysed to release hemoglobin into the sample mixture, and the released hemoglobin forms a chromogen with the ligand. Then, the sample mixture is delivered from the first conduit into the flow channel 560 of the flow-through cuvette 500. The sample mixture fills in the entire flow channel 560, with a portion thereof flowing out from the second conduit. Then, the flow of the sample mixture is stopped for a short period of time, typically a few seconds, and the intensity of the transmitted light through the measurement segment 566 is measured by the photo detector 50. After the measurement, the sample mixture is flushed out from the flow channel, either by delivering a cleaning solution from the first conduit, or delivering the cleaning solution from the second conduit to push the sample mixture back from the first conduit. After cleaning, the flow-through cuvette is ready for measurement of another blood sample.

The obtained intensity is used to calculate hemoglobin concentration of the blood sample according to Beer's law. Methods of spectrophotometric measurement of hemoglobin concentration of a blood sample are known in the art. In general, the calculation involves volumes of the blood sample and the lytic reagent and any other additional reagent used in diluting the blood sample, the absorption coefficient of the chromogen to be measured, the optical length of the measurement, the intensity of the transmitted light measured from the sample mixture, and the intensity of the transmitted light measured from a blank (typically measured from a diluent in the absence of the blood sample). The spectrophotometer can be calibrated with a calibrator that has a known hemoglobin concentration. Once calibrated, hemoglobin concentration of the blood sample analyzed on the hematology analyzer is calculated automatically.

As can be appreciated, the miniature flow-through cuvette of the present invention and the spectrophotometer including such a cuvette have solved several challenging technical problems in small sample volume analysis, particularly in near patient clinical diagnostic tests. First, by using the length, rather than the width or diameter, of the measurement segment of the flow channel as the optical length for optical measurement, the diameter of the flow channel is substantially reduced to achieve a significant reduction in overall volume of the channel in the cuvette and in associated conduits within a measurement device, while maintaining a sufficient optical length for accurate spectrophotometric measurement. As a result, in the miniature cuvette of the present invention the volume of the entire flow channel is preferably only from about 10 μl to about 60 μl. This is particularly suitable for near patient hematology test, where a very small volume of peripheral blood collected by a fingerstick of a patient can be used to provide an accurate measurement. Moreover, the miniature size uses only small volumes of the reagents used for the measurement and the cleaning solution used for cleaning the flow channel, as such it renders feasible to provide reagents and cleaning solution and to prepare a sample mixture within a disposable reagent cassette or cartridge. Both of these are desirable in near patient tests.

Second, by orienting the interface segments of the flow channel generally in the vertical direction, the structure effectively reduces micro-bubble accumulation in the measurement segment wherein the optical measured is made. Third, by providing the inclined inner surfaces in the two turning segments and eliminating sharp turn corners between the interface segments and the measurement segment, the miniature cuvette facilitates a smooth flow of a liquid sample throughout the flow channel, and eliminates micro-bubble formation at the dead spots. Fourth, in addition to eliminating the dead spots since the interface segments and the measurement segment have a substantially same diameter, fluid restriction within the flow channel is minimized. In combination, these structural features effectively minimize micro-bubble formation and accumulation in the flow channel, particularly in the measurement segment when a liquid sample passes through the cuvette. This successfully minimizes or prevents interference of micro-bubbles to the absorption measurement of the sample mixture in the cuvette, and prevents potential errors caused by micro-bubbles in hemoglobin measurement of a blood sample in clinical diagnostic tests. Furthermore, it has been found that with the miniature cuvette of the present invention, only a small volume of a cleaning solution is sufficient to clean the flow channel of the cuvette and maintain the surface of the flow channel free of micro-bubbles for repetitive and long term use.

Fifth, by further providing proper degrees of inclination of the inclined planar inner surfaces, as well as the outer surfaces as needed, according to the optical relationship between the material and the liquid sample, the measurement segment of the flow channel is optically aligned with the incident light and the photo detector. This reduces light scattering and reflection along the light path and improves accuracy of the spectrophotometric measurement.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A flow-through cuvette for spectrophotometric measurement of a liquid sample comprising:
    a first and a second body block, each body block having an inclined planar outer surface and an opposing joining surface; said first and second body blocks joined together forming a cuvette body, with said joining surfaces of said body blocks disposed directly against each other and said inclined planar outer surfaces opposing each other; and
    a flow channel through said cuvette body, said flow channel formed by joining two separate portions in sequence into a continuous channel, each portion formed integrally within one of said body blocks; said flow channel comprising a first interface segment in the first body block and a second interface segment in the second body block, oriented generally in a direction of a vertical axis of said cuvette body, each thereof having an open exit; a measurement segment between the first and second interface segments, oriented generally horizontally with a central axis thereof in transverse to said joining surfaces of said body blocks, and said measurement segment formed by connecting, in alignment, a first and a second portion thereof in the first and the second body block, respectively, when said joining surfaces of said body blocks are joined together; a first inclined planar inner surface disposed in a first turning segment between the first interface segment and the first portion of said measurement segment, facing the planar outer surface of the first body block; and an opposing second inclined planar inner surface disposed in a second turning segment between the second interface segment and the second portion of said measurement segment, facing the planar outer surface of the second body block; said first and second inclined planar inner surfaces intercepting said central axis of the measurement segment and terminating said measurement segment at opposing ends thereof, thereby permitting light linearly passing said measurement segment through said first and second inclined planar inner surfaces for said spectrophotometric measurement;
    said first and second body blocks made of a transparent material by molding, each body block forming one single piece structure with an uninterrupted integral structure of said inclined inner surfaces in said flow channel and said inclined planar outer surfaces in each body block.

2. The flow-through cuvette of claim 1, wherein each of said first and second body blocks comprises a sealing groove on said joining surfaces of said body blocks, surrounding respective portion of said measurement segment of said flow channel; and a sealing member is disposed in said sealing grooves.

3. The flow-through cuvette of claim 2, wherein the sealing member is an O-ring made of an elastic material.

4. The flow-through cuvette of claim 1, wherein said joining surfaces are painted with a dark color to reduce light scattering in a light path along said measurement segment.

5. The flow-through cuvette of claim 1, wherein each of said first and second body blocks comprises a pair of flange, adapted to fasten said body blocks.

6. The flow-through cuvette of claim 1, wherein an inclined angle of each of said first and second inclined planar inner surfaces relative to said vertical axis is from about 15 to about 65 degrees.

7. The flow-through cuvette of claim 6, wherein said planar outer surfaces of said body blocks have an inclined angle relative to said vertical axis different from an inclined angle of corresponding inclined planar inner surface relative to said vertical axis.

8. The flow-through cuvette of claim 1, wherein each of said first and second interface segments of said flow channel has a longitudinal axis thereof from about 80 to about 135 degrees relative to said central axis of said measurement segment.

9. The flow-through cuvette of claim 1, wherein said first and second interface segments and said measurement segment have a substantially same diameter.

10. The flow-through cuvette of claim 1, wherein said measurement segment of said flow channel has a length from about 4 mm to about 25 mm, and a diameter from about 0.8 mm to about 4.0 mm.

11. A spectrophotometer for measurement of a liquid sample in a flow-through cuvette comprising:
    (a) a flow-through cuvette comprising a first and a second body block, each body block having an inclined planar outer surface and an opposing joining surface; said first and second body blocks joined together forming a cuvette body, with said joining surfaces of said body blocks disposed directly against each other and said inclined planar outer surfaces opposing each other; and a flow channel through said cuvette body, said flow channel formed by joining two separate portions in sequence into a continuous channel, each portion formed integrally within one of said body blocks; said flow channel comprising a first interface segment in the first body block and a second interface segment in the second body block, oriented generally in a direction of a vertical axis of said cuvette body, each thereof having an open exit; a measurement segment between the first and second interface segments, oriented generally horizontally, with a central axis thereof in transverse to said joining surfaces of said body blocks, and said measurement segment formed by connecting, in alignment, a first and a second portion thereof in the first and the second body block, respectively, when said joining surfaces of said body blocks are joined together; a first inclined planar inner surface disposed in a first turning segment between the first interface segment and the first portion of said measurement segment, facing the planar outer surface of the first body block; and an opposing second inclined planar inner surface disposed in a second turning segment between the second interface segment and the second portion of said measurement segment, facing the planar outer surface of the second body block; said first and second inclined planar inner surfaces intercepting said central axis of the measurement segment and terminating said measurement segment at opposing ends thereof, thereby permitting light linearly passing said measurement segment through said first and second inclined planar inner surfaces for said spectrophotometric measurement; said first and second body blocks made of a transparent material by molding, each body block forming one single piece structure with an uninterrupted integral structure of said inclined inner surfaces in said flow channel and said inclined planar outer surfaces in each body block;

(b) a light source disposed next to the inclined planar outer surface of the first body block and adapted to emit an incident light beam through said measurement segment of said flow channel; and (c) a photodetector disposed next to the inclined planar outer surface of the second body block and adapted to receive a transmitted light through said measurement segment of said flow channel.

12. The spectrophotometer of claim 11, wherein said light source comprises a housing having a chamber of a dark interior and a light outlet positioned against the planar outer surface of the first body block, and a light bulb disposed within said housing, facing said light outlet.

13. The spectrophotometer of claim 12, wherein said light outlet has a dimension less than a dimension of said first inclined planar inner surface of said flow channel of said flow-through cuvette.

14. The spectrophotometer of claim 13, wherein a center of said light outlet of said light source is optically aligned with said central axis of said measurement segment of said flow channel of said flow-through cuvette.

15. The spectrophotometer of claim 11, wherein said photodetector comprises a detector housing having a chamber of a dark interior and a light inlet positioned against said planar outer surface of the second body block, and a sensor disposed within said detector housing.

16. The spectrophotometer of claim 15, wherein a center of said light inlet of said photodetector is optically aligned with said central axis of said measurement segment of said flow channel of said flow-through cuvette.

17. The spectrophotometer of claim 11, wherein each of said first and second body blocks of the flow-through cuvette comprises a sealing groove on said joining surfaces of said body blocks, surrounding respective portion of said measurement segment of said flow channel; and a sealing member is disposed in said sealing grooves.

18. The spectrophotometer of claim 17, wherein the sealing member is an O-ring made of an elastic material.

19. The spectrophotometer of claim 11, wherein said joining surfaces of said first and second body blocks of the flow-through cuvette are painted with a dark color to reduce light scattering in a light path along said measurement segment.

20. The spectrophotometer of claim 11, wherein each of said first and second body blocks of the flow-through cuvette comprises a pair of flanges, adapted to fasten said body blocks.

* * * * *